(12) United States Patent
Farwick et al.

(10) Patent No.: US 7,049,106 B2
(45) Date of Patent: May 23, 2006

(54) PROCESS FOR THE PRODUCTION OF L-AMINO ACIDS BY FERMENTATION USING CORYNEFORM BACTERIA WITH AN ATTENUATED MQO GENE

(75) Inventors: Mike Farwick, Bielefeld (DE); Brigitte Bathe, Salzkotten (DE); Thomas Hermann, Bielefeld (DE); Achim Marx, Halle (DE); Walter Pfefferle, Halle (DE)

(73) Assignee: Degussa AG, Hanau-Wolfgang (DE)

( * ) Notice: Subject to any disclaimer, the term of this patent is extended or adjusted under 35 U.S.C. 154(b) by 323 days.

(21) Appl. No.: 10/118,325

(22) Filed: Apr. 9, 2002

(65) Prior Publication Data

US 2003/0044943 A1 Mar. 6, 2003

Related U.S. Application Data

(60) Provisional application No. 60/352,212, filed on Jan. 29, 2002.

(30) Foreign Application Priority Data

Apr. 10, 2001 (DE) ................ 101 17 816

(51) Int. Cl.
 *C12P 13/04* (2006.01)
(52) U.S. Cl. ...................... 435/106; 435/115
(58) Field of Classification Search ............... 435/106, 435/115
See application file for complete search history.

(56) References Cited

FOREIGN PATENT DOCUMENTS

| EP | 1 038 969 A2 | 9/2000 |
| EP | 1 085 091 A1 | 3/2001 |
| WO | WO 03/029457 A1 * | 4/2003 |

OTHER PUBLICATIONS

Molenaar et al., "Functions of the Membrane-Associated and Cytoplasmic Malate Dehydrogenases in the Citric Acid Cycle of *Corynebacterium glutamicum*", vol. 182, No. 24, pp. 6884-6891, Dec. 2000.

van der Rest et al., "Functions of the Membrane-Associated and Cytoplasmic Malate Dehydrogenases in the Citric Acid Cycle of *Escherichia coli*", vol. 182, No. 24, pp. 6892-6899, Dec. 2000.

Molenaar et al., "Biochemical and genetic characterization of the membrane-associated malate dehydrogenase (acceptor) from *Corynebacterium glutamicum*", vol. 254, pp. 395-403, Jan. 1998.

* cited by examiner

*Primary Examiner*—Kathleen Kerr
(74) *Attorney, Agent, or Firm*—Venable LLP; Ann S. Hobbs

(57) ABSTRACT

A process for the production of an L-amino acid wherein coryneform bacteria (e.g. *Coryneform glutamicum*) in which expression of the mqo gene coding for malate quinone oxidoreductase is attenuated are fermented to produce a desired amino acid, and the amino acid is concentrated in the medium or cells and isolated. Optionally, further genes in the biosynthetic pathway of the desired amino acid are enhanced, and/or metabolic pathways that reduce formation of the amino acid are suppressed.

6 Claims, 2 Drawing Sheets

Figure 1: pXK99Emob
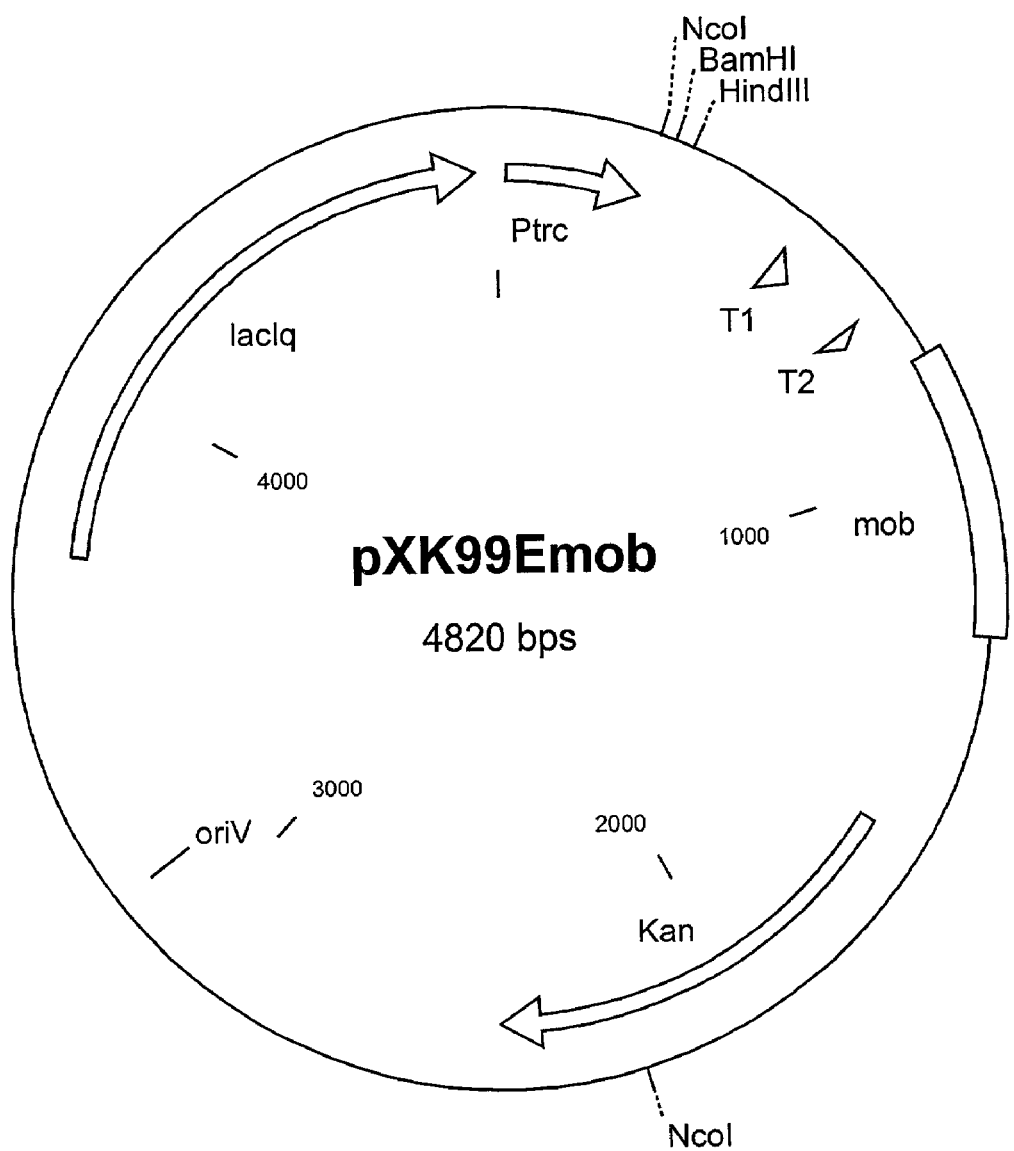

Figure 2: pXK99Emobmqo
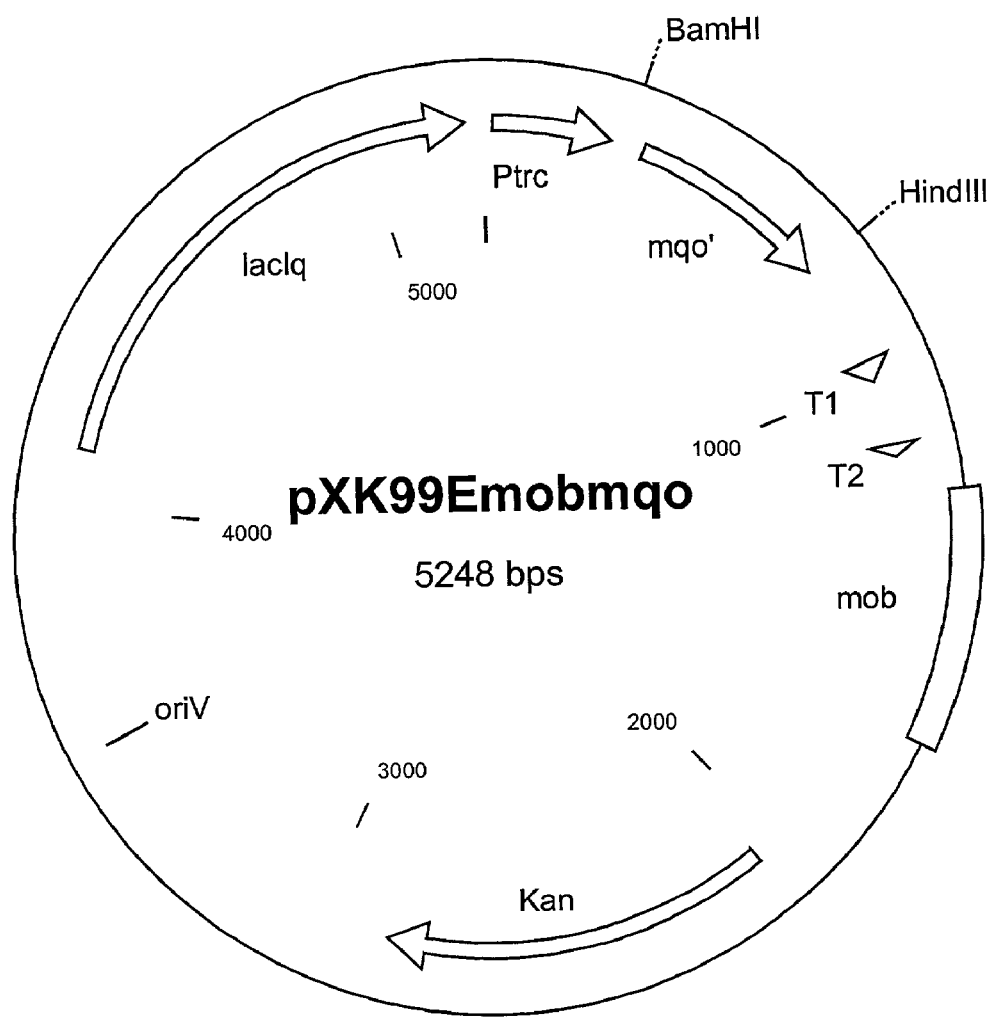

US 7,049,106 B2

PROCESS FOR THE PRODUCTION OF L-AMINO ACIDS BY FERMENTATION USING CORYNEFORM BACTERIA WITH AN ATTENUATED MQO GENE

CROSS REFERENCE TO RELATED APPLICATIONS

This application claims priority to German application DE 101 17 816.6, filed Apr. 10, 2001, and U.S. Provisional application No. 60/352,212, filed Jan. 29, 2002, each of which is incorporated herein by reference in its entirety.

FIELD OF THE INVENTION

The invention provides a process for the production of L-amino acids, especially L-lysine, by fermentation using coryneform bacteria in which the mqo gene, which codes for malate quinone oxidoreductase, has been attenuated.

BACKGROUND INFORMATION

L-amino acids, especially L-lysine, are used in human medicine and in the pharmaceuticals industry, in the foodstuffs industry and, very especially, in the feeding of animals.

It is known that amino acids are produced by fermentation of strains of coryneform bacteria, especially *Corynebacterium glutamicum*. Because of their great importance, attempts are continuously being made to improve the production processes. Improvements to the processes may concern measures relating to the fermentation, such as, for example, stirring and oxygen supply, or the composition of the nutrient media, such as, for example, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are employed. Such methods yield strains which are resistant to antimetabolites, such as, for example, the lysine analogue S-(2-aminoethyl)-cysteine, or are auxotrophic for metabolites that are important in terms of regulation, and which produce L-amino acids.

For a number of years, methods of recombinant DNA technology have also been used for improving the strain of L-amino acid-producing strains of *Corynebacterium glutamicum*, by amplifying individual amino acid biosynthesis genes and studying the effect on L-amino acid production.

SUMMARY OF THE INVENTION

Object of the Invention

In EP-A-1038969 it is described that an improvement in the production of L-amino acids by fermentation can be achieved by enhancement, especially overexpression, of the mqo gene.

The inventors have set themselves the object of providing novel bases for improved processes for the production of L-amino acids, especially L-lysine, by fermentation using coryneform bacteria.

DESCRIPTION OF THE INVENTION

Where L-amino acids or amino acids are mentioned hereinbelow, they are to be understood as meaning one or more amino acids, including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-lysine is particularly preferred.

Where L-lysine or lysine is mentioned hereinbelow, it is to be understood as meaning not only the bases but also the salts, such as, for example, lysine monohydrochloride or lysine sulfate.

The invention provides a process for the production of L-amino acids by fermentation using coryneform bacteria in which at least the nucleotide sequence coding for malate quinone oxidoreductase (mqo gene) is attenuated, especially excluded or expressed at a low level.

This invention also provides a process for the production of L-amino acids by fermentation in which the following steps are carried out:

a) fermentation of the L-amino acid-producing coryneform bacteria in which at least the nucleotide sequence coding for malate quinone oxidoreductase is attenuated, especially excluded or expressed at a low level;

b) concentration of the L-amino acids in the medium or in the cells of the bacteria; and c) isolation of the desired L-amino acids, in which optionally portions or the entirety of the constituents of the fermentation liquor and/or of the biomass remain in the end product.

The strains used preferably produce L-amino acids, especially L-lysine, even before attenuation of the mqo gene.

Preferred embodiments are to be found in the claims.

The term "attenuation" or "attenuate" in this context describes the diminution or exclusion of the intracellular activity of one or more enzymes (proteins) in a microorganism that are coded for by the corresponding DNA, by, for example, using a weak promoter or using a gene or allele that codes for a corresponding enzyme having a low level of activity, or by inactivating the corresponding gene or enzyme (protein), and optionally by combining those measures.

The microorganisms provided by the present invention are able to produce amino acids from glucose, saccharose, lactose, fructose, maltose, molasses, starch, cellulose or from glycerol and ethanol. They may be representatives of coryneform bacteria, especially of the genus *Corynebacterium*. In the case of the genus *Corynebacterium*, special mention may be made of the species *Corynebacterium glutamicum*, which is known to those skilled in the art for its ability to produce L-amino acids.

Suitable strains of the genus *Corynebacterium*, especially of the species *Corynebacterium glutamicum*, are especially the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-amino acid-producing mutants or strains prepared therefrom such as, for example, the L-lysine-producing strains
Corynebacterium glutamicum FERM-P 1709
Brevibacterium flavum FERM-P 1708
Brevibacterium lactofermentum FERM-P 1712
Corynebacterium glutamicum FERM-P 6463
Corynebacterium glutamicum FERM-P 6464
Corynebacterium glutamicum ATCC 21513
Corynebacterium glutamicum ATCC 21544
Corynebacterium glutamicum ATCC 21543
Corynebacterium glutamicum DSM 4697 and
Corynebacterium glutamicum DSM 5715.

Contrary to the prior art (EP-A-1038969) it has been found that coryneform bacteria produce L-amino acids in an improved manner after attenuation of the mqo gene.

The nucleotide sequence of the mqo gene of *Corynebacterium glutamicum* has been published by Molenar et al. (European Journal of Biochemistry 254, 395–403 (1998)) and can also be taken from the gene library under Accession Number AJ 22 4946. The nucleotide sequence is also shown in SEQ ID No. 1 and the amino acid sequence of the protein is shown in SEQ ID No. 2.

The sequences described in the mentioned references coding for malate quinone oxidoreductase can be used according to the invention. It is also possible to use alleles of malate quinone oxidoreductase, which are formed from the degeneracy of the genetic code or by sense mutations that are neutral in terms of function.

In order to achieve attenuation, either the expression of the mqo gene or the catalytic properties of the gene products can be diminished or excluded. The two measures are optionally combined.

Gene expression can be diminished by carrying out the culturing in a suitable manner or by genetic alteration (mutation) of the signal structures of gene expression. Signal structures of gene expression are, for example, repressor genes, activator genes, operators, promoters, attenuators, ribosome-binding sites, the start codon and terminators. The person skilled in the art will find information thereon, for example, in patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), and in known textbooks of genetics and molecular biology, such as, for example, the textbook of Knippers ("Molekulare Genetik", 6th edition, Georg Thieme Verlag, Stuttgart, Germany, 1995) or that of Winnacker ("Gene und Klone", VCH Verlagsgesellschaft, Weinheim, Germany, 1990).

Mutations that lead to a change in or diminution of the catalytic properties of enzyme proteins are known from the prior art; examples which may be mentioned are the works of Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms", Berichte des Forschungszentrums Jülichs,Jül-2906, ISSN09442952, Jülich, Germany, 1994). Summaries are to be found in known textbooks of genetics and molecular biology, such as, for example, that of Hagemann ("Allgemeine Genetik", Gustav Fischer Verlag, Stuttgart, 1986).

There come into consideration as mutations transitions, transversions, insertions and deletions. In dependence on the effect of the amino acid substitution on the enzyme activity, missense mutations or nonsense mutations are referred to. Insertions or deletions of at least one base pair in a gene lead to frame shift mutations, as a result of which incorrect amino acids are incorporated or the translation breaks off prematurely. If a stop codon forms in the coding region as the result of a mutation, that likewise generally leads to premature breaking off of the translation.

Deletions of several codons typically lead to complete loss of enzyme activity. Instructions for the production of such mutations are part of the prior art and can be found in known textbooks of genetics and molecular biology, such as, for example, the textbook of Knippers ("Molekulare Genetik", 6th edition, Georg Thieme Verlag, Stuttgart, Germany, 1995), that of Winnacker ("Gene und Klone", VCH Verlagsgesellschaft, Weinheim, Germany, 1990) or that of Hagemann ("Allgemeine Genetik", Gustav Fischer Verlag, Stuttgart, 1986).

The invention provides the allele 672, shown in SEQ ID No. 3, of the mqo gene, which allele carries the nucleotide adenine instead of the nucleotide guanine at position 672 of the DNA sequence (see SEQ ID No. 1), which leads to substitution of the TGG codon coding for the amino acid tryptophan-224 (see SEQ ID No. 2) by an opal (TGA) stop codon.

The invention also provides the allele 1230, shown in SEQ ID No. 4, of the mqo gene, which allele carries the nucleotide adenine instead of the nucleotide guanine at position 672 of the DNA sequence (see SEQ ID No. 1), which leads to substitution of the tgg codon coding for the amino acid tryptophan-224 (see SEQ ID No. 2) by an opal stop codon and which additionally carries a nucleotide substitution at position 1230 of cytosine to thymine.

A common method of mutating genes of *C. glutamicum* is the method of gene disruption and of gene replacement described by Schwarzer and Pühler (Bio/Technology 9, 84–87 (1991)).

In the method of gene disruption, a central portion of the coding region of the gene in question is cloned into a plasmid vector which is able to replicate in a host (typically *E. coli*), but not in *C. glutamicum*. Suitable vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–5465 (1992)), pGEM-T (Promega corporation, Madison, Wis., USA), pCR2.1-TOPO (Shuman (1994). Journal of Biological Chemistry 269:32678–32684; U.S. Pat. No. 5,487,993), pCR®Blunt (Invitrogen, Groningen, Netherlands; Bernard et al., Journal of Molecular Biology, 234: 534–541 (1993)) or pEM1 (Schrumpf et al., 1991, Journal of Bacteriology 173:4510–4516). The plasmid vector containing the central portion of the coding region of the gene is then transferred to the desired strain of *C. glutamicum* by conjugation or transformation. The method of conjugation is described, for example, in Schäfer et al. (Applied and Environmental Microbiology 60, 756–759 (1994)). Methods of transformation are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a cross-over occurrence, the coding region of the gene in question is disrupted by the vector sequence, and two incomplete alleles lacking the 3'- and the 5'-end, respectively, are obtained. That method has been used, for example, by Fitzpatrick et al. (Applied Microbiology and Biotechnology 42, 575–580 (1994)) to exclude the recA gene of *C. glutamicum*.

In the gene replacement method, a mutation, such as, for example, a deletion, insertion or base substitution, is produced in vitro in the gene in question. The allele that is produced is in turn cloned into a vector that is not replicative for *C. glutamicum,* and the latter is then transferred to the desired host of *C. glutamicum* by transformation or conjugation. After homologous recombination by means of a first cross-over occurrence effecting integration and by means of a suitable second cross-over occurrence effecting an excision in the target gene or in the target sequence, incorporation of the mutation or of the allele is achieved.

That method has been used, for example, by Peters-Wendisch et al. (Microbiology 144, 915–927 (1998)) to exclude the pyc gene of *C. glutamicum* by means of a deletion. That method has been used by Schäfer et al. (Gene 145: 69–73 (1994)), for example, in order to incorporate a deletion into the hom-thrB gene region. In the same way, a deletion has been introduced into the cgl gene region of *C. glutamicum* by Schäfer et al. (Journal of Bacteriology 176: 7309–7319 (1994)).

A deletion, insertion or a base substitution can thus be incorporated into the mqo gene.

In addition, it may be advantageous for the production of L-amino acids, in addition to attenuating the mqo gene, to enhance, especially to overexpress, one or more enzymes of the biosynthesis pathway in question, of glycolysis, of the anaplerotic pathway, of the citric acid cycle, of the pentose phosphate cycle, of amino acid export, and optionally regulatory proteins.

The term "enhancement" or "enhance" in this context describes an increase in the intracellular activity of one or more enzymes or proteins in a microorganism that are coded for by the corresponding DNA, by, for example, increasing the number of copies of the gene or genes, using a strong promoter or a gene or allele that codes for a corresponding enzyme or protein having a high level of activity, and optionally by combining those measures.

Accordingly, for the production of L-lysine, in addition to attenuating the mqo gene, one or more genes selected from the group the gene lysC coding for a feed-back resistant aspartate kinase (Accession No. P26512, EP-B-0387527; EP-A-0699759; WO 00/63388), the gene dapA coding for dihydrodipicolinate synthase (EP-B 0 197 335), the gene gap coding for glyceraldehyde-3-phosphate dehydrogenase (Eikmanns (1992). Journal of Bacteriology 174:6076–6086), at the same time the gene pyc coding for pyruvate carboxylase (DE-A-198 31 609), the gene zwf coding for glucose-6-phosphate dehydrogenase (JP-A-09224661), at the same time the gene lysE coding for lysine export (DE-A-195 48 222), the gene zwa1 coding for the Zwa1 protein (DE: 19959328.0, DSM 13115)

the gene tpi coding for triose phosphate isomerase (Eikmanns (1992), Journal of Bacteriology 174:6076–6086), and the gene pgk coding for 3-phosphoglycerate kinase (Eikmanns (1992), Journal of Bacteriology 174:6076–6086), can be enhanced, especially overexpressed.

It may also be advantageous for the production of amino acids, especially L-lysine, in addition to attenuating the mqo gene, at the same time to attenuate, especially to diminish the expression of, one or more genes selected from the group the gene pck coding for phosphoenol pyruvate carboxykinase (DE 199 50 409.1, DSM 13047), the gene pgi coding for glucose-6-phosphate isomerase (U.S. Pat. No. 6,586,214, DSM 12969), the gene poxB coding for pyruvate oxidase (DE:1995 1975.7, DSM 13114), the gene zwa2 coding for the Zwa2 protein (DE: 19959327.2, DSM 13113).

Finally, it may be advantageous for the production of amino acids, in addition to attenuating the mqo gene, to exclude undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention also form part of the invention and can be cultivated, for the purposes of the production of L-amino acids, continuously or discontinuously by the batch process or by the fed batch or repeated fed batch process. A summary of known cultivation methods is described in the textbook of Chmiel (Bioprozesstechnik 1. Einführung in die Bioverfahrenstechnik (Gustav Fischer Verlag, Stuttgart, 1991)) or in the textbook of Storhas (Bioreaktoren und periphere Einrichtungen (Vieweg Verlag, Braunschweig/Wiesbaden, 1994)).

The culture medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981).

There may be used as the carbon source sugars and carbohydrates, such as, for example, glucose, saccharose, lactose, fructose, maltose, molasses, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid. Those substances may be used individually or in the form of a mixture.

There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture.

There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be fed in in a suitable manner during the cultivation.

In order to control the pH value of the culture, basic compounds, such as sodium hydroxide, potassium hydroxide, ammonia or ammonia water, or acid compounds, such as phosphoric acid or sulfuric acid, are expediently used. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of the desired product has formed. That aim is normally achieved within a period of from 10 hours to 160 hours.

Methods of determining L-amino acids are known from the prior art. The analysis may be carried out as described in Spackman et al. (Analytical Chemistry, 30, (1958), 1190) by anion-exchange chromatography with subsequent ninhydrin derivatization, or it may be carried out by reversed phase HPLC, as described in Lindroth et al. (Analytical Chemistry (1979) 51: 1167–1174).

BRIEF DESCRIPTION OF THE DRAWINGS:

FIG. 1: Map of the plasmid pXK99Emob,
FIG. 2: Map of the plasmid pXK99Emobmqo.
The abbreviations and designations used have the following meaning.

| Kan: | Kanamycin resistance gene aph (3') -IIa from *Escherichia coli* |
|---|---|
| BamHI | Cleavage site of the restriction enzyme BamHI |
| HindIII | Cleavage site of the restriction enzyme HindIII |
| NcoI | Cleavage site of the restriction enzyme NcoI |
| Ptrc | trc promoter |
| T1 | Termination region T1 |
| T2 | Termination region T2 |
| lacIq | lacIq repressor of the lac operon of *Escherichia coli* |
| oriV | Replication origin ColE1 from *E. coli* |
| mob | RP4-mobilization site |
| mqo | Cloned region of the mqo gene |

DETAILED DESCRIPTION OF THE INVENTION

The present invention is explained in more detail in the following using working examples.

EXAMPLE 1

Preparation of the Vector pXK99Emobmqo 1.1 Cloning of the mqo gene

From the strain ATCC 13032, chromosomal DNA was isolated by the method of Eikmanns et al. (Microbiology 140: 1817–1828 (1994)). On the basis of the sequence of the mqo gene known for *C. glutamicum*, the following oligonucleotides were chosen for the polymerase chain reaction (see SEQ ID No. 5 and SEQ ID No. 6):

```
mqo_oP1:
5'- GA GGA TCC GCA GAG AAC TCG CGG AGA TA-3' mqo_hind:
5'- CT AAG CTT CGT AGC GAG CCT TGA TGT AT-3'
```

The primers were chosen here so that the amplified fragment contains the incomplete gene, starting with the native ribosome binding site without the promoter region, and the front region of the mqo gene. Furthermore, the primer mqo$_{oP}$1 contains the sequence for the cleavage site of the restriction endonuclease BamHI, and the primer mqo_hind the cleavage site of the restriction endonuclease HindIII, which are marked by underlining in the nucleotide sequence shown above.

The primers shown were synthesized by MWG-Biotech AG (Ebersberg, Germany) and the PCR reaction was carried out by the standard PCR method of Innis et al. (PCR protocols. A guide to methods and applications, 1990, Academic Press) with Pwo-Polymerase from Roche Diagnostics GmbH (Mannheim, Germany). With the aid of the polymerase chain reaction, the primers allow amplification of a DNA fragment 468 bp in size, which carries the incomplete mqo gene, including the native ribosome binding site.

The mqo fragment 468 bp in size was cleaved with the restriction endonucleases BamHI and HindIII and then isolated from the agarose gel with the QiaExII Gel Extraction Kit (Product No. 20021, Qiagen, Hilden, Germany).

1.2 Construction of the Vector pXK99Emob

The IPTG-inducible expression vector pXK99Emob was constructed according to the prior art. The vector is based on the *Escherichia coli* expression vector pTRC99A (Amann et al., Gene 69: 301–315 (1988)) and contains the trc promoter, which can be induced by addition of the lactose derivative IPTG (isopropyl β-D-thiogalactopyranoside), the termination regions T1 and T2, the replication origin ColE1 from *E. Coli*, the lacI$^q$ gene (repressor of the lac operon from *E.coli*), a multiple cloning site (mcs) (Norrander, J. M. et al. Gene 26, 101–106 (1983)), the kanamycin resistance gene aph (3')-IIa from *E. coli* (Beck et al. (1982), Gene 19: 327–336) and the RP4-mobilization-site from the cloning vector pK18mobsacB (Schaefer et al, Gene 14: 69–73 (1994).

It has been found that the vector pXK99Emob is quite specifically suitable for regulating the expression of a gene, in particular effecting attenuated expression in coryneform bacteria. The vector pXK99Emob is an *E. coli* expression vector and can be employed in *E. coli* for enhanced expression of a gene.

Since the vector cannot replicate independently in coryneform bacteria, this is retained in the cell only if it is integrated into the chromosome. The peculiarity of this vector here is the use for regulated expression of a gene after cloning of a gene section from the front region of the corresponding gene in the vector containing the start codon and the native ribosome binding site, and subsequent integration of the vector into coryneform bacteria, in particular *C. glutamicum*. Gene expression is regulated by addition of metered amounts of IPTG to the nutrient medium. Amounts of 0.5 µM up to 10 µM IPTG have the effect of very weak expression of the corresponding gene, and amounts of 10 µM up to 100 µM have the effect of a slightly attenuated to normal expression of the corresponding gene.

The *E. coli* expression vector pXK99Emob constructed was transferred by means of electroporation (Tauch et al. 1994, FEMS Microbiol Letters, 123: 343–347) into *E. coli* DH5αmcr (Grant, 1990, Proceedings of the National Academy of Sciences U.S.A., 87:4645–4649). Selection of the transformants was carried out on LB Agar (Sambrook et al., Molecular Cloning: A Laboratory Manual. 2$^{nd}$ Ed., Cold Spring Harbor Laboratory Press, Cold Spring Harbor, N.Y., 1989), which had been supplemented with 50 mg/l kanamycin.

Plasmid DNA was isolated from a transformant by conventional methods (Peters-Wendisch et al., 1998, Microbiology, 144, 915–927), cleaved with the restriction endonuclease NcoI, and the plasmid was checked by subsequent agarose gel electrophoresis.

The plasmid construct obtained in this way was called pXK99Emob (FIG. 1). The strain obtained by electroporation of the plasmid pXK99Emob in the *E. coli* strain DH5αmcr was called *E. coli* DH5alphamcr/pXK99Emob.

1.3 Cloning of the mqo Fragment into Vector pXK99Emob

The *E. coli* expression vector pXK99Emob described in Example 1.2 was used as the vector. DNA of this plasmid was cleaved completely with the restriction enzymes BamHI and HindIII and then dephosphorylated with shrimp alkaline phosphatase (Roche Diagnostics GmbH, Mannheim, Germany, Product Description SAP, Product No. 1758250).

The mqo fragment approx. 458 bp in size described in 1.1, obtained by means of PCR and cleaved with the restriction endonucleases BamHI and HindIII was mixed with the prepared vector pXK99Emob and the batch was treated with T4 DNA ligase (Amersham Pharmacia, Freiburg, Germany, Product Description T4-DNA-Ligase, Code No. 27-0870-04). The ligation batch was transformed in the *E. coli* strain DH5αmcr (Hanahan, In: DNA cloning. A Practical Approach. Vol. I, IRL-Press, Oxford, Washington DC, USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes BamHI and HindIII to check the plasmid by subsequent agarose gel electrophoresis. The resulting plasmid was called pXK99Emobmqo. It is shown in FIG. 2.

The following microorganism was deposited as a pure culture on 15th February 2002 at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* DH5alphamcr/pXK99Emobmqo (=DH5αmcr/pXK99Emobmqo) as DSM 14815.

EXAMPLE 2

Integration of the Vector pXK99Emobmqo into the genome of the *C. glutamicum* Strain DSM5715

The vector pXK99Emobmqo mentioned in Example 1 was electroporated by the electroporation method of Tauch et al.,(1989 FEMS Microbiology Letters 123: 343–347) in the strain *C. glutamicum* DSM5715. The vector cannot replicate independently in DSM5715 and is retained in the cell only if it has integrated into the chromosome. Selection of clones with integrated pXK99Emobmqo was carried out by plating out the electroporation batch on LB agar (Sambrook et al., Molecular Cloning: A Laboratory Manual. $2_{nd}$ Ed., Cold Spring Harbor, N.Y., 1989), which had been supplemented with 15 mg/l kanamycin and IPTG (1mM).

A selected kanamycin-resistant clone which has the Plasmid pXK99Emobmqo, mentioned in Example 1, inserted in the chromosomal mqo-gene of DSM5715, was called DSM5715::pXK99Emobmqo.

EXAMPLE 3

Preparation of Lysine

The *C. glutamicum* strain DSM5715::pXK99Emobmqo obtained in Example 2 was cultured in a nutrient medium suitable for the production of lysine and the lysine content in the culture supernatant was determined. By addition of IPTG, attenuated expression of the mqo gene occurs, regulated by the trc promoter.

For this, the strain was first incubated on an agar plate with the corresponding antibiotic (brain-heart agar with kanamycin (25 mg/l) and IPTG (10 μM)) for 24 hours at 330° C. Starting from this agar plate culture, a preculture was seeded (10 ml medium in a 100 ml conical flask). The complete medium Cg III was used as the medium for the preculture.

| Medium Cg III | |
| --- | --- |
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) and IPTG (10 μM) were added to this. The preculture was incubated for 16 hours at 330° C. at 240 rpm on a shaking machine. The OD (660 nm) of the preculture was 0.5. 500 μl of this preculture were transinoculated into a main culture. By transfer of IPTG-containing medium from the preculture, the IPTG concentration in the main culture was approx. 0.5 μM. Medium MM was used for the main culture.

| Medium MM | |
| --- | --- |
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution are brought to pH 7 with aqueous ammonia and autoclaved. The sterile substrate and vitamin solutions are then added, and the $CaCO_3$ autoclaved in the dry state is added.

Culturing was carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Lysine HCl g/l |
| --- | --- | --- |
| DSM5715 | 6.8 | 12.82 |
| DSM5715::pXK99Emobmqo | 6.4 | 14.85 |

What is claimed is:

1. A process for the production of one or more L-amino acids comprising the following steps:
   a) fermenting *Corynebacterium glutamicum* in which expression of at least the endogenous mqo gene coding for malate quinone oxidoreductase is eliminated by mutagenesis,
   b) accumulating at least one L-amino acid in the medium or in the cells of the bacteria, and
   c) isolating the L-amino acid(s) as an end product in which optionally portions or the entirety of the constituents of the fermentation liquor and/or of the biomass remain in the end product.

2. The process according to claim 1, wherein said L-amino acid is L-lysine.

3. The process of claim 1, wherein said elimination of expression is achieved by a method of mutagenesis selected from the group consisting of:
   a) insertion of at least one base pair,
   b) deletion of at least one base pair,
   c) transition mutagenesis generating a stop codon, and
   d) transversion mutagenesis generating a stop codon.

4. The process of claim 3, wherein said method of mutagenesis generates an opal stop codon.

5. The process of claim 4, wherein said opal stop codon is at a position in the nucleic acid comprising the sequence of SEQ ID NO:1 which codes for the tryptophan residue of position 224 of the protein of SEQ ID NO:2.

6. The process of claim 5, wherein said method of mutagenesis alters said mqo gene to the sequence set forth in SEQ ID NO:3 or in SEQ ID NO:4.

* * * * *

SEQUENCE LISTING

<160> NUMBER OF SEQ ID NOS: 6

<210> SEQ ID NO 1
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo-gene

<400> SEQUENCE: 1

| | | | | | | | | | | | | | | | | |
|---|---|---|---|---|---|---|---|---|---|---|---|---|---|---|---|---|
| atg | tca | gat | tcc | ccg | aag | aac | gca | ccg | agg | att | acc | gat | gag | gca | gat | 48 |
| Met | Ser | Asp | Ser | Pro | Lys | Asn | Ala | Pro | Arg | Ile | Thr | Asp | Glu | Ala | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gta | gtt | ctc | att | ggt | gcc | ggt | atc | atg | agc | tcc | acg | ctg | ggt | gca | atg | 96 |
| Val | Val | Leu | Ile | Gly | Ala | Gly | Ile | Met | Ser | Ser | Thr | Leu | Gly | Ala | Met | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | cgt | cag | ctg | gag | cca | agc | tgg | act | cag | atc | gtc | ttc | gag | cgt | ttg | 144 |
| Leu | Arg | Gln | Leu | Glu | Pro | Ser | Trp | Thr | Gln | Ile | Val | Phe | Glu | Arg | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| gat | gga | ccg | gca | caa | gag | tcg | tcc | tcc | ccg | tgg | aac | aat | gca | gga | acc | 192 |
| Asp | Gly | Pro | Ala | Gln | Glu | Ser | Ser | Ser | Pro | Trp | Asn | Asn | Ala | Gly | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| ggc | cac | tct | gct | cta | tgc | gag | ctg | aac | tac | acc | cca | gag | gtt | aag | ggc | 240 |
| Gly | His | Ser | Ala | Leu | Cys | Glu | Leu | Asn | Tyr | Thr | Pro | Glu | Val | Lys | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aag | gtt | gaa | att | gcc | aag | gct | gta | gga | atc | aac | gag | aag | ttc | cag | gtt | 288 |
| Lys | Val | Glu | Ile | Ala | Lys | Ala | Val | Gly | Ile | Asn | Glu | Lys | Phe | Gln | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| tcc | cgt | cag | ttc | tgg | tct | cac | ctc | gtt | gaa | gag | gga | gtg | ctg | tct | gat | 336 |
| Ser | Arg | Gln | Phe | Trp | Ser | His | Leu | Val | Glu | Glu | Gly | Val | Leu | Ser | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| cct | aag | gaa | ttc | atc | aac | cct | gtt | cct | cac | gta | tct | ttc | ggc | cag | ggc | 384 |
| Pro | Lys | Glu | Phe | Ile | Asn | Pro | Val | Pro | His | Val | Ser | Phe | Gly | Gln | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| gca | gat | cag | gtt | gca | tac | atc | aag | gct | cgc | tac | gaa | gct | ttg | aag | gat | 432 |
| Ala | Asp | Gln | Val | Ala | Tyr | Ile | Lys | Ala | Arg | Tyr | Glu | Ala | Leu | Lys | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| cac | cca | ctc | ttc | cag | ggc | atg | acc | tac | gct | gac | gat | gaa | gct | acc | ttc | 480 |
| His | Pro | Leu | Phe | Gln | Gly | Met | Thr | Tyr | Ala | Asp | Asp | Glu | Ala | Thr | Phe | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| acc | gag | aag | ctg | cct | ttg | atg | gca | aag | ggc | cgt | gac | ttc | tct | gat | cca | 528 |
| Thr | Glu | Lys | Leu | Pro | Leu | Met | Ala | Lys | Gly | Arg | Asp | Phe | Ser | Asp | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| gta | gca | atc | tct | tgg | atc | gat | gaa | ggc | acc | gac | atc | aac | tac | ggt | gct | 576 |
| Val | Ala | Ile | Ser | Trp | Ile | Asp | Glu | Gly | Thr | Asp | Ile | Asn | Tyr | Gly | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | acc | aag | cag | tac | ctg | gat | gca | gct | gaa | gtt | gaa | ggc | act | gaa | atc | 624 |
| Gln | Thr | Lys | Gln | Tyr | Leu | Asp | Ala | Ala | Glu | Val | Glu | Gly | Thr | Glu | Ile | |
| | | | 195 | | | | | 200 | | | | | 205 | | | |

| | | | | | | | | | | | | | | | | |
|---|---|---|---|---|---|---|---|---|---|---|---|---|---|---|---|---|
| cgc | tat | ggc | cac | gaa | gtc | aag | agc | atc | aag | gct | gat | ggc | gca | aag | tgg | 672 |
| Arg | Tyr | Gly | His | Glu | Val | Lys | Ser | Ile | Lys | Ala | Asp | Gly | Ala | Lys | Trp | |
| | 210 | | | | | 215 | | | | | 220 | | | | | |

| | | | | | | | | | | | | | | | | |
|---|---|---|---|---|---|---|---|---|---|---|---|---|---|---|---|---|
| atc | gtg | acc | gtc | aag | aac | gta | cac | act | ggc | gac | acc | aag | acc | atc | aag | 720 |
| Ile | Val | Thr | Val | Lys | Asn | Val | His | Thr | Gly | Asp | Thr | Lys | Thr | Ile | Lys | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| gca | aac | ttc | gtg | ttc | gtc | ggc | gca | gga | gga | tac | gca | ctg | gat | ctg | ctt | 768 |
| Ala | Asn | Phe | Val | Phe | Val | Gly | Ala | Gly | Gly | Tyr | Ala | Leu | Asp | Leu | Leu | |
| | | | | 245 | | | | | 250 | | | | | 255 | | |

```
cgc agc gca ggc atc cca cag gtc aag ggc ttc gct gga ttc cca gta    816
Arg Ser Ala Gly Ile Pro Gln Val Lys Gly Phe Ala Gly Phe Pro Val
        260                 265                 270 tcc ggc ctg tgg ctt cgt tgc acc aac gag gaa ctg atc gag cag cac    864
Ser Gly Leu Trp Leu Arg Cys Thr Asn Glu Glu Leu Ile Glu Gln His
    275                 280                 285 gca gcc aag gta tat ggc aag gca tct gtt ggc gct cct cca atg tct    912
Ala Ala Lys Val Tyr Gly Lys Ala Ser Val Gly Ala Pro Pro Met Ser
290                 295                 300 gtt cct cac ctt gac acc cgc gtt atc gag ggt gaa aag ggt ctg ctc    960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc   1008
Phe Gly Pro Tyr Gly Gly Trp Thr Pro Lys Phe Leu Lys Glu Gly Ser
                325                 330                 335 tac ctg gac ctg ttc aag tcc atc cgc cca gac aac att cct tcc tac   1056
Tyr Leu Asp Leu Phe Lys Ser Ile Arg Pro Asp Asn Ile Pro Ser Tyr
            340                 345                 350 ctt ggc gtt gct gct cag gaa ttt gat ctg acc aag tac ctt gtc act   1104
Leu Gly Val Ala Ala Gln Glu Phe Asp Leu Thr Lys Tyr Leu Val Thr
        355                 360                 365 gaa gtt ctc aag gac cag gac aag cgt atg gat gct ctt cgc gag tac   1152
Glu Val Leu Lys Asp Gln Asp Lys Arg Met Asp Ala Leu Arg Glu Tyr
    370                 375                 380 atg cca gag gca caa aac ggc gat tgg gag acc atc gtt gcc gga cag   1200
Met Pro Glu Ala Gln Asn Gly Asp Trp Glu Thr Ile Val Ala Gly Gln
385                 390                 395                 400 cgt gtt cag gtt att aag cct gca gga ttc cct aag ttc ggt tcc ctg   1248
Arg Val Gln Val Ile Lys Pro Ala Gly Phe Pro Lys Phe Gly Ser Leu
                405                 410                 415 gaa ttc ggc acc acc ttg atc aac aac tcc gaa ggc acc atc gcc gga   1296
Glu Phe Gly Thr Thr Leu Ile Asn Asn Ser Glu Gly Thr Ile Ala Gly
            420                 425                 430 ttg ctc ggt gct tcc cct gga gca tcc atc gca cct tcc gca atg atc   1344
Leu Leu Gly Ala Ser Pro Gly Ala Ser Ile Ala Pro Ser Ala Met Ile
        435                 440                 445 gag ctg ctt gag cgt tgc ttc ggt gac cgc atg atc gag tgg ggc gac   1392
Glu Leu Leu Glu Arg Cys Phe Gly Asp Arg Met Ile Glu Trp Gly Asp
    450                 455                 460 aag ctg aag gac atg atc cct tcc tac ggc aag aag ctt gct tcc gag   1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag   1488
Pro Ala Leu Phe Glu Gln Gln Trp Ala Arg Thr Gln Lys Thr Leu Lys
                485                 490                 495 ctt gag gaa gcc taa                                               1503
Leu Glu Glu Ala
            500

<210> SEQ ID NO 2
<211> LENGTH: 500
<212> TYPE: PRT
<213> ORGANISM: Corynebacterium glutamicum

<400> SEQUENCE: 2

Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
            20                  25                  30
```

-continued

```
Leu Arg Gln Leu Glu Pro Ser Trp Thr Gln Ile Val Phe Glu Arg Leu
        35                  40                  45

Asp Gly Pro Ala Gln Glu Ser Ser Pro Trp Asn Asn Ala Gly Thr
 50                  55                  60

Gly His Ser Ala Leu Cys Glu Leu Asn Tyr Thr Pro Glu Val Lys Gly
 65                  70                  75                  80

Lys Val Glu Ile Ala Lys Ala Val Gly Ile Asn Glu Lys Phe Gln Val
                 85                  90                  95

Ser Arg Gln Phe Trp Ser His Leu Val Glu Glu Gly Val Leu Ser Asp
                100                 105                 110

Pro Lys Glu Phe Ile Asn Pro Val Pro His Val Ser Phe Gly Gln Gly
            115                 120                 125

Ala Asp Gln Val Ala Tyr Ile Lys Ala Arg Tyr Glu Ala Leu Lys Asp
    130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ala Glu Val Glu Gly Thr Glu Ile
        195                 200                 205

Arg Tyr Gly His Glu Val Lys Ser Ile Lys Ala Asp Gly Ala Lys Trp
    210                 215                 220

Ile Val Thr Val Lys Asn Val His Thr Gly Asp Thr Lys Thr Ile Lys
225                 230                 235                 240

Ala Asn Phe Val Phe Val Gly Ala Gly Gly Tyr Ala Leu Asp Leu Leu
                245                 250                 255

Arg Ser Ala Gly Ile Pro Gln Val Lys Gly Phe Ala Gly Phe Pro Val
            260                 265                 270

Ser Gly Leu Trp Leu Arg Cys Thr Asn Glu Glu Leu Ile Glu Gln His
        275                 280                 285

Ala Ala Lys Val Tyr Gly Lys Ala Ser Val Gly Ala Pro Pro Met Ser
    290                 295                 300

Val Pro His Leu Asp Thr Arg Val Ile Glu Gly Glu Lys Gly Leu Leu
305                 310                 315                 320

Phe Gly Pro Tyr Gly Gly Trp Thr Pro Lys Phe Leu Lys Glu Gly Ser
                325                 330                 335

Tyr Leu Asp Leu Phe Lys Ser Ile Arg Pro Asp Asn Ile Pro Ser Tyr
            340                 345                 350

Leu Gly Val Ala Ala Gln Glu Phe Asp Leu Thr Lys Tyr Leu Val Thr
        355                 360                 365

Glu Val Leu Lys Asp Gln Asp Lys Arg Met Asp Ala Leu Arg Glu Tyr
    370                 375                 380

Met Pro Glu Ala Gln Asn Gly Asp Trp Glu Thr Ile Val Ala Gly Gln
385                 390                 395                 400

Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
        435                 440                 445

Glu Leu Leu Glu Arg Cys Phe Gly Asp Arg Met Ile Glu Trp Gly Asp
```

-continued

```
                450                 455                 460
Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
            500

<210> SEQ ID NO 3
<211> LENGTH: 1503
<212> TYPE: DNA
<213> ORGANISM: Corynebacterium glutamicum
<220> FEATURE:
<221> NAME/KEY: -
<222> LOCATION: (1)..(1500)
<223> OTHER INFORMATION: mqo-allele 672
<220> FEATURE:
<221> NAME/KEY: misc_feature
<222> LOCATION: (1)..(3)
<223> OTHER INFORMATION: start-codon
<220> FEATURE:
<221> NAME/KEY: misc_feature
<222> LOCATION: (670)..(672)
<223> OTHER INFORMATION: opal stop-codon

<400> SEQUENCE: 3
atgtcagatt ccccgaagaa cgcaccgagg attaccgatg aggcagatgt agttctcatt     60
ggtgccggta tcatgagctc cacgctgggt gcaatgctgc gtcagctgga gccaagctgg    120
actcagatcg tcttcgagcg tttggatgga ccggcacaag agtcgtcctc cccgtggaac    180
aatgcaggaa ccggccactc tgctctatgc gagctgaact acaccccaga ggttaagggc    240
aaggttgaaa ttgccaaggc tgtaggaatc aacgagaagt tccaggtttc ccgtcagttc    300
tggtctcacc tcgttgaaga gggagtgctg tctgatccta aggaattcat caaccctgtt    360
cctcacgtat ctttcggcca gggcgcagat caggttgcat acatcaaggc tcgctacgaa    420
gctttgaagg atcacccact cttccagggc atgacctacg ctgacgatga agctaccttc    480
accgagaagc tgcctttgat ggcaaagggc cgtgacttct ctgatccagt agcaatctct    540
tggatcgatg aaggcaccga catcaactac ggtgctcaga ccaagcagta cctggatgca    600
gctgaagttg aaggcactga aatccgctat ggccacgaag tcaagagcat caaggctgat    660
ggcgcaaagt gaatcgtgac cgtcaagaac gtacacactg gcgacaccaa gaccatcaag    720
gcaaacttcg tgttcgtcgg cgcaggcgga tacgcactgg atctgcttcg cagcgcaggc    780
atcccacagg tcaagggctt cgctggattc ccagtatccg gcctgtggct tcgttgcacc    840
aacgaggaac tgatcgagca gcacgcagcc aaggtatatg caaggcatc tgttggcgct    900 cctccaatgt ctgttcctca ccttgacacc cgcgttatcg agggtgaaaa gggtctgctc    960
tttggacctt acggtggctg gacccctaag ttcttgaagg aaggctccta cctggacctg   1020
ttcaagtcca tccgcccaga caacattcct tcctaccttg gcgttgctgc tcaggaattt   1080
gatctgacca gtaccttgt cactgaagtt ctcaaggacc aggacaagcg tatggatgct   1140
cttcgcgagt acatgccaga ggcacaaaac ggcgattggg agaccatcgt tgccggacag   1200
cgtgttcagg ttattaagcc tgcaggattc cctaagttcg gttccctgga attcggcacc   1260
accttgatca acaactccga aggcaccatc gccggattgc tcggtgcttc ccctggagca   1320
tccatcgcac cttccgcaat gatcgagctg cttgagcgtt gcttcggtga ccgcatgatc   1380
gagtggggcg acaagctgaa ggacatgatc ccttcctacg caagaagct tgcttccgag   1440
```

```
ccagcactgt tgagcagca gtgggcacgc acccagaaga ccctgaagct tgaggaagcc      1500
taa                                                                  1503

<210> SEQ ID NO 4
<211> LENGTH: 1503
<212> TYPE: DNA
<213> ORGANISM: Corynebacterium glutamicum
<220> FEATURE:
<221> NAME/KEY: -
<222> LOCATION: (1)..(1500)
<223> OTHER INFORMATION: mqo-allele 1230
<220> FEATURE:
<221> NAME/KEY: misc_feature
<222> LOCATION: (1)..(3)
<223> OTHER INFORMATION: start-codon
<220> FEATURE:
<221> NAME/KEY: misc_feature
<222> LOCATION: (670)..(672)
<223> OTHER INFORMATION: opal stop-codon
<220> FEATURE:
<221> NAME/KEY: misc_feature
<222> LOCATION: (1230)..(672)
<223> OTHER INFORMATION: C-T transition

<400> SEQUENCE: 4
atgtcagatt ccccgaagaa cgcaccgagg attaccgatg aggcagatgt agttctcatt      60
ggtgccggta tcatgagctc cacgctgggt gcaatgctgc gtcagctgga gccaagctgg     120
actcagatcg tcttcgagcg tttggatgga ccggcacaag agtcgtcctc ccgtggaac      180 aatgcaggaa ccggccactc tgctctatgc gagctgaact acaccccaga ggttaagggc     240
aaggttgaaa ttgccaaggc tgtaggaatc aacgagaagt tccaggtttc ccgtcagttc     300
tggtctcacc tcgttgaaga gggagtgctg tctgatccta aggaattcat caaccctgtt     360
cctcacgtat ctttcggcca gggcgcagat caggttgcat acatcaaggc tcgctacgaa     420 gcttttgaagg atcaccccact cttccagggc atgacctacg ctgacgatga agctaccttc     480
accgagaagc tgcctttgat ggcaaagggc cgtgacttct ctgatccagt agcaatctct     540
tggatcgatg aaggcaccga catcaactac ggtgctcaga ccaagcagta cctggatgca     600
gctgaagttg aaggcactga aatccgctat ggccacgaag tcaagagcat caaggctgat     660
ggcgcaaagt gaatcgtgac cgtcaagaac gtacacactg cgacaccaa gaccatcaag      720 gcaaacttcg tgttcgtcgg cgcaggcgga tacgcactgg atctgcttcg cagcgcaggc     780
atcccacagg tcaagggctt cgctggattc ccagtatccg gcctgtggct tcgttgcacc     840
aacgaggaac tgatcgagca gcacgcagcc aaggtatatg caaggcatc tgttggcgct     900 cctccaatgt ctgttcctca ccttgacacc cgcgttatcg agggtgaaaa gggtctgctc     960
tttggacctt acggtggctg accctaag ttcttgaagg aaggctccta cctgacctg      1020 ttcaagtcca tccgcccaga caacattcct tcctaccttg gcgttgctgc tcaggaattt     1080
gatctgacca agtaccttgt cactgaagtt ctcaaggacc aggacaagcg tatggatgct     1140
cttcgcgagt acatgccaga ggcacaaaac ggcgattggg agaccatcgt tgccggacag     1200
cgtgttcagg ttattaagcc tgcaggattt cctaagttcg gttccctgga attcggcacc     1260
accttgatca caactccga aggcaccatc gccggattgc tcggtgcttc ccctggagca     1320
tccatcgcac cttccgcaat gatcgagctg cttgagcgtt gcttcggtga ccgcatgatc     1380
gagtggggcg acaagctgaa ggacatgatc ccttcctacg caagaagct tgcttccgag     1440 ccagcactgt tgagcagca gtgggcacgc acccagaaga ccctgaagct tgaggaagcc     1500
taa                                                                  1503
```

```
<210> SEQ ID NO 5
<211> LENGTH: 28
<212> TYPE: DNA
<213> ORGANISM: artificial sequence
<220> FEATURE:
<223> OTHER INFORMATION: Primer containing restriction enzyme site
<220> FEATURE:
<221> NAME/KEY: misc_feature
<222> LOCATION: (1)..(28)
<223> OTHER INFORMATION: Primer mqo_oP1

<400> SEQUENCE: 5
gaggatccgc agagaactcg cggagata                                            28

<210> SEQ ID NO 6
<211> LENGTH: 28
<212> TYPE: DNA
<213> ORGANISM: artificial sequence
<220> FEATURE:
<223> OTHER INFORMATION: Primer containing restriction enzyme site
<220> FEATURE:
<221> NAME/KEY: misc_feature
<222> LOCATION: (1)..(28)
<223> OTHER INFORMATION: Primer mqo_hind

<400> SEQUENCE: 6
ctaagcttcg tagcgagcct tgatgtat                                            28
```